(12) United States Patent
Schramm, Jr.

(10) Patent No.: US 7,623,621 B1
(45) Date of Patent: Nov. 24, 2009

(54) METHOD AND SYSTEM FOR IDENTIFYING AND AUTHENTICATING AN OBJECT

(75) Inventor: Harry F. Schramm, Jr., Winchester, TN (US)

(73) Assignee: The United States of America as represented by the Administrator of the National Aeronautics and Space Administration, Washington, DC (US)

( * ) Notice: Subject to any disclaimer, the term of this patent is extended or adjusted under 35 U.S.C. 154(b) by 0 days.

(21) Appl. No.: 12/047,686

(22) Filed: Mar. 13, 2008

(51) Int. Cl.
*G01N 23/223* (2006.01)
(52) U.S. Cl. .......................................... 378/44
(58) Field of Classification Search ............. 378/44, 378/45, 49
See application file for complete search history.

(56) References Cited

U.S. PATENT DOCUMENTS

| | | | |
|---|---|---|---|
| 4,445,225 A | 4/1984 | White | |
| 6,032,856 A | 3/2000 | Bischoff et al. | |
| 6,359,962 B1 * | 3/2002 | Yagi | 378/44 |
| 6,501,825 B2 | 12/2002 | Kaiser et al. | |
| 6,616,051 B1 | 9/2003 | Zidon | |
| 6,688,789 B2 | 2/2004 | Oshima et al. | |
| 6,801,595 B2 | 10/2004 | Grodzins et al. | |
| 6,850,592 B2 | 2/2005 | Schramm et al. | |
| 7,017,812 B1 * | 3/2006 | Schramm et al. | 235/454 |
| 2003/0194052 A1 | 10/2003 | Price et al. | |
| 2005/0276906 A1 * | 12/2005 | Metzger | 427/7 |
| 2006/0086901 A1 | 4/2006 | Price et al. | |
| 2007/0058775 A1 * | 3/2007 | Benderly | 378/45 |

* cited by examiner

*Primary Examiner*—Chih-Cheng G Kao
(74) *Attorney, Agent, or Firm*—James J. McGroary; Peter J. Van Bergen

(57) ABSTRACT

An object has a taggant placed in a first portion thereof and has a visible symbol placed on a second portion thereof. When the object is to be identified and authenticated, the taggant is made to radiate with a specific energy signature. The energy signature and at least one image of the symbol are recorded along with a relative location that identifies the first portion of the object. The combination of the energy signature, symbol image and relative location are used to repeatedly identify and authenticate the object.

22 Claims, 1 Drawing Sheet

Figure 1:
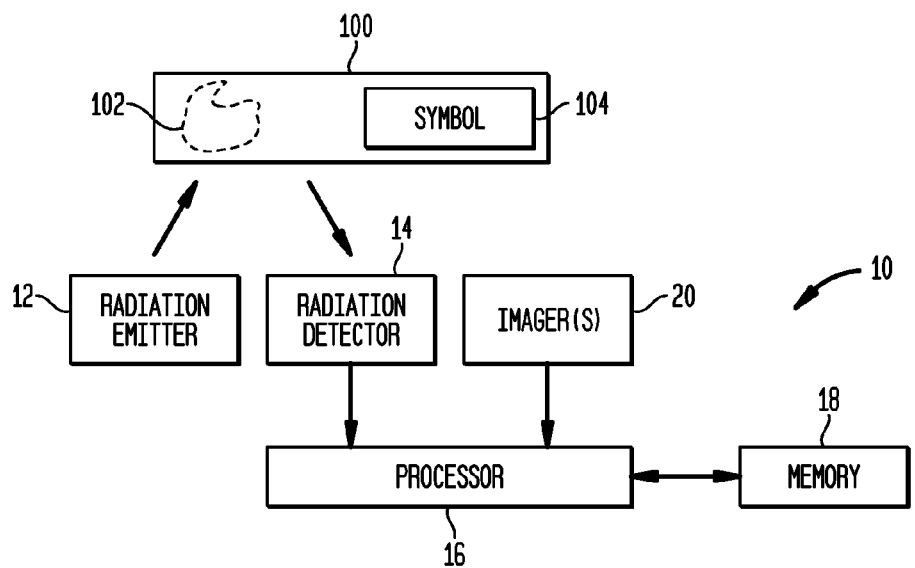

METHOD AND SYSTEM FOR IDENTIFYING AND AUTHENTICATING AN OBJECT

ORIGIN OF THE INVENTION

The invention was made by an employee of the United States Government and may be manufactured and used by or for the Government for governmental purposes without the payment of any royalties.

BACKGROUND OF THE INVENTION

1. Field of the Invention

This invention relates to methods and systems for identification and authentication. More specifically, the invention is a method and system for identifying and authenticating an object using both x-ray fluorescence and visible symbol imaging.

2. Description of the Related Art

Object marking for purpose of object identification comes in a variety of forms. Visible, optically-read marks such as bar codes and data matrix symbols are used in commercial, government, and military applications. Numerous visible-marking and detection systems are known in the art. Invisible markings or "taggants" are used when an object must be covertly marked for later verification or authentication by a specialized detection system. "Invisible" taggants can be realized by, for example, nanoparticles contained in a clear coating or covered by a protective coating. The invisible taggants are trace deposits of one or more elements that are detected and analyzed. For example, the taggants can include elements that fluoresce when exposed to x-rays. The x-ray fluorescent spectrum of the taggant serves as the object identifier. However, even with these known technologies, there is still a need in the art of object marking, identification and authentication for a system/method that allows an object to be readily identified and authenticated at different points in time with a high degree of confidence.

SUMMARY OF THE INVENTION

Accordingly, it is an object of the present invention to provide a method and system for identifying and authenticating an object.

Another object of the present invention is to provide a method and system for identifying and authenticating an object at different points in time with high degree of confidence.

Other objects and advantages of the present invention will become more obvious hereinafter in the specification and drawings.

In accordance with the present invention, a method and system for identifying and authenticating an object are provided. The object has a taggant placed in a first portion thereof and has a visible symbol placed on a second portion thereof. When the object is to be identified and authenticated, the taggant is made to radiate with a specific energy signature. The energy signature and at least one image of the symbol are recorded. In addition, a relative location identifying the first portion of the object is recorded. The combination of the energy signature, symbol image and relative location can be used to repeatedly identify and authenticate the object.

BRIEF DESCRIPTION OF THE DRAWING(S)

Figure 2:
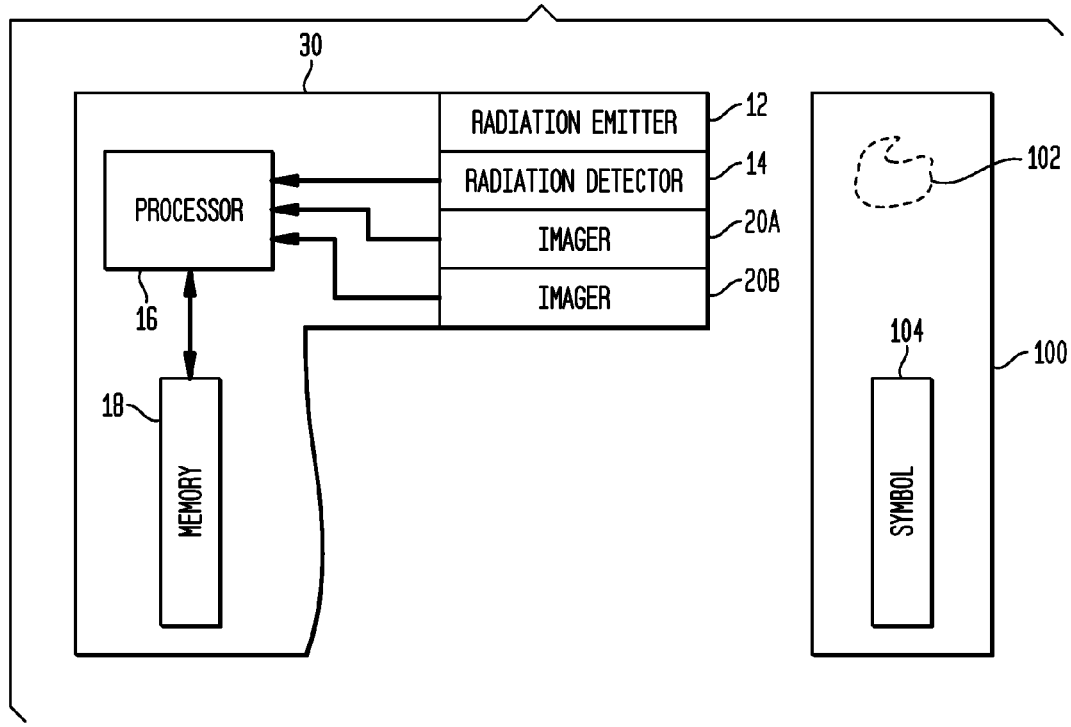

Other objects, features and advantages of the present invention will become apparent upon reference to the following description of the preferred embodiments and to the drawings, wherein corresponding reference characters indicate corresponding parts throughout the several views of the drawings and wherein:

FIG. 1 is a schematic view of a system for identifying and authenticating an object in accordance with the present invention; and FIG. 2 is a schematic view of a hand-held version of the system in accordance with an embodiment of the present invention.

DESCRIPTION OF THE PREFERRED EMBODIMENT(S)

Referring now to the drawings and more particularly to FIG. 1, a system for identifying and authenticating an object 100 in accordance with the present invention is shown and is referenced generally by numeral 10. Object 100 is any physical part, product, structure, etc., that can support the inclusion of an invisible taggant 102 and a visible symbol 104. Taggant 102 and symbol 104 are spatially separated from one another as illustrated. The amount of separation can vary based on the size of the object 100 and/or the field-of-view of system 10 as will be explained later below. Taggant 102 and symbol 104 uniquely identify object 100 and will be used to verify the authenticity thereof in accordance with the present invention.

Taggant 102 is representative of one or more taggant materials that radiate a detectable energy signature when activated. The taggant(s) can be incorporated in object 100 using any suitable technique. Many existing tagging techniques involve the use of microparticles or nanoparticles containing the elements, or compounds or compositions of the elements, that comprise the taggant(s). Additionally, particles can be manufactured where smaller particles, or compounds or compositions of the elements, contain the taggant. Such particles could be made of magnetic or fluorescent material to facilitate detection, refractory materials to enhance particle survival in an explosion, or chemically inert materials to enhance particle survival in a chemical reaction. Indeed, such particles could be made of nondurable, soluble, or reactive materials to enhance taggant dispersal in a fluid, aerosol, or powder system.

Taggant 102 can be inserted into the object either during or after the object (or a part thereof) has been manufactured. During manufacture, the taggant can be incorporated into any location (including surfaces) of the object. Two (and three) dimensional amorphous shapes or specific patterns of the taggant(s) can be constructed using any desired combination of types and numbers of taggants.

Taggant(s) incorporated after manufacture of the object could, for example, be incorporated into the already-formed object as a dopant. Additionally, the taggant can be implanted into the object or deposited as coating or film on the object. As a coating or film, the taggant could be physically or chemically deposited by itself. The taggant could also be incorporated as one ingredient (or contaminant) of another material (such as a mixture or solution) that forms a coating or film. In this aspect of the invention, the taggant can be incorporated as an element or compound in solution (or suspension) with a liquid which is applied, such as by spraying, to the object. For example, the taggant could be dissolved or suspended in a solvent so that when that solvent evaporates after being applied to the object, the residue left behind would contain the taggant.

If taggant 102 is one that fluoresces when exposed to x-ray radiation, the present invention can use x-ray fluorescence analysis to detect at least one elemental taggant that has been extrinsically added to the object. With x-ray fluorescence (XRF) analysis, x-rays are produced from electron shifts in the inner shell(s) of atoms of the taggants and, therefore are not affected by the form (chemical bonding) of the object being analyzed. The x-rays' spectral signature identifies where that specific taggant is present in the object. Accordingly, identification and authentication system 10 includes a radiation (e.g., x-ray) emitter 12 and a radiation detector 14. The energy signature detected by detector 14 is passed to a processor 16 for further processing/analysis. For example, processor 16 could convert the detected energy signature into a format (e.g., ASCII) that will simplify subsequent comparative processing in accordance with the present invention as will be explained further below. An exemplary XRF system for accomplishing the above-described functions of emitter 12, detector 14 and processor 16 is described in U.S. Pat. No. 6,850,592, the contents of which are hereby incorporated by reference.

In the present invention, the energy signature (radiated by taggant 102) in a preferred electronic format is stored in a memory 18. A date/time stamp could also be stored with the energy signature data. In addition, the "signature" of the person responsible for generating/recording the energy signature data could be stored.

Identification and authentication system 10 also includes one or more imagers 20 for capturing an image of symbol 104 that is any visible symbol on object 100. Symbol 104 can be any two-dimensional marking (e.g., bar code, data matrix, etc.) that can be coupled to object 100. For example, symbol 104 can be painted/coated on object 104, affixed to object 104 by way of a label or tag, etc. Symbol 104 could also be any three-dimensional marking that is molded, cast, forged, engraved, embossed, stamped, etched, or otherwise incorporated into object 104 in a visible manner.

Imager(s) 20 are any imaging device(s) capable of recording an image of symbol 104 that permits analysis thereof by processor 16. For example, if symbol 104 is a bar code or data matrix symbol, imager(s) 20 must be able to read and resolve the details of symbol 104 such that processor 16 can decode/convert symbol 104 to a suitable format (e.g., ASCII or other format compatible with the electronic data version of the energy signature associated with taggant 102) for processing. A variety of such imaging systems are well known in the art. For low contrast situations, imager(s) 20 can include a variable-distance angular symbology reader disclosed in U.S. Pat. No. 7,017,812, the contents of which are hereby incorporated by reference.

In addition, to having a field-of-view that can suitably focus on symbol 104, imager(s) 20 must record an image that can be used to identify the relative location of taggant 102. That is, to ensure repeatability of measurement, the relative location of taggant 102 must be recorded by system 10 each time taggant 102 and symbol 104 are read. If taggant 102 and symbol 104 are read simultaneously, the relative location of taggant 102 can be recorded as a position on object 100 relative to symbol 104, a readily-identifiable reference point on object 100, or both. The relative location of taggant 102 can be stored in memory 18 along with the taggant's energy signature and data associated with symbol 104. The relative location can be memorialized in a variety of ways without departing from the scope of the present invention. For example, relative location could be recorded pictorially or by a coordinate map as would be well understood in the art of image processing.

At some point later in time, when object 100 is to be identified/authenticated, system 10 is again used to "read" both taggant 102 and symbol 104 as described above. The currently-recorded taggant energy signature symbol data and relative location are compared (at processor 16) with the data stored in memory 18. Verification of the identification of object 100 is provided via symbol 104 while authentication of object 100 is provided via the energy signature and relative location of taggant 102. The data regarding the relative location of taggant 102 ensures that the repeatability of the identification and authentication process.

System 10 can be realized by a variety of hardware and software arrangements without departing from the scope of the present invention. For example, the elements of system 10 can be included in a single device that can be hand-held, mounted on a handling system, mounted on a robot, etc. By way of example, a hand-held version of system 10 is illustrated in FIG. 2 where two imagers 20A and 20B are coupled to hand-held housing 30. Imager 20A is designed to read and resolve symbol 104 while imager 20B has a wider field-of-view so that it can "see" symbol 104 and the portion of object 100 that includes taggant 102 so that a relative location of taggant 102 can be determined. As described above, the data is stored in memory 18 that can be a fixed or removable memory.

The advantages of the present invention are numerous. Covert and visible symbol markings are read/recorded simultaneously to provide a repeatable and secure object identification and authentication system and method. The visible symbol provides unique and readily understood object identification. The covert taggant and its relative location provide the means to repeatedly authenticate the object. The covert taggant could also be used for identification. In cases where visible symbols have not or cannot be applied to an object, the taggant and reference location can be used to identify and authenticate an object.

The present invention can be utilized in a wide variety of commercial, government, and military applications. It can be used during manufacturing and in post-manufacturing situations. The present invention can be configured as a fixed device, a hand-held device, or a miniaturized device (e.g., a borescope type system). Several aerospace applications could utilize the present invention. For example, the present invention could be used as a device that works with a robot end effector when authentication of parts using humans is not possible. For example, parts could have been involved in an accident and could be contaminated with certain hazardous or radioactive materials. Robots are commonly sent into such perilous situations to avoid injury to humans. One example of this in use would be on the Shuttle launch pad with work that must be done in the event of a leaking substance such as hydrazine. If a robotic device were sent to do damage assessment, the current invention would be able to read part numbers and authenticate materials in question.

Another aerospace application for the present invention involves robotic devices sent to the moon or other planets to investigate the surface thereof. That is, the present invention could perform real-time analysis of the materials found on and slightly below the surface. The XRF would enable analysis in certain ranges in order to identify most of the materials of interest for habitat construction and nuclear fuel production. The imaging with graphical registration or coordinate registration would provide the ability for the robot to return to the exact location where an XRF analysis was preformed previously and repeat the test. Although this is not an authentication application in the same manner as parts identification, it uses the same coordinate mapping for authentication to a location for certain repeatability.

Finally, the aerospace and aeronautical communities are susceptible to counterfeit parts that find their way into critical assemblies. The present invention can be used to safeguard against counterfeit parts. It can also safeguard against other types of unapproved parts, such as life expended parts that are sold for scrap, cleaned up by unscrupulous vendors, and then resold as new parts.

Although the invention has been described relative to a specific embodiment thereof, there are numerous variations and modifications that will be readily apparent to those skilled in the art in light of the above teachings. It is therefore to be understood that, within the scope of the appended claims, the invention may be practiced other than as specifically described.

What is claimed as new and desired to be secured by Letters Patent of the United States is:

1. A method of identifying and authenticating an object, comprising the steps of:
   placing a taggant in a first portion of an object;
   placing a symbol on a second portion of the object;
   causing said taggant to radiate with a specific energy signature;
   recording said energy signature and at least one image of said symbol to include (i) a first image of said symbol using a first field-of-view that is substantially limited to said symbol, and (ii) a second image of said symbol using a second field-of-view that includes said symbol and said first portion of the object; and
   recording a relative location of the first portion of the object.

2. A method according to claim 1 wherein said taggant fluoresces.

3. A method according to claim 1 wherein said symbol is a two-dimensional symbol.

4. A method according to claim 1 wherein said step of causing comprises the step of impinging x-rays on the object in the vicinity of the first portion thereof.

5. A method according to claim 1 wherein said steps of recording occur simultaneously.

6. A method according to claim 1 wherein said relative location is relative to at least one of a position on the object and said symbol.

7. A method according to claim 1 further comprising the steps of:
   converting said energy signature and said image of said symbol to electronic data in a compatible data format; and
   storing said electronic data and said relative location.

8. A method according to claim 7 wherein said steps of causing, recording and converting occur at a first time, said method further comprising the steps of:
   repeating said steps of causing, recording and converting at a second time that is subsequent to said first time, wherein a current relative location is recorded and a current electronic data is generated at said second time; and
   comparing said electronic data and said second time; and
   comparing said electronic data and said relative location from said first time with said current electronic data and said current relative location from said second time.

9. A method according to claim 8 wherein said steps of causing, recording, converting, storing, repeating and comparing are performed using a single device.

10. A method according to claim 7 wherein said steps of causing, recording, converting and storing are performed using a single device.

11. A method according to claim 1 wherein said steps of causing and recording are performed using a single device.

12. A method of identifying and authenticating an object, comprising the steps of:
    placing an x-ray fluorescing taggant in a first portion of an object;
    placing a visible symbol on a second portion of the object;
    directing x-rays at the object wherein said taggant fluoresces with a specific energy signature; and
    recording said energy signature, at least one image of said visible symbol, and a relative location of the first portion of the object, wherein said at least one image of said visible symbol includes (i) a first image of said visible symbol in a first field-of-view that is substantially limited to said visible symbol, and (ii) a second image of said visible symbol in a second field-of-view that includes said visible symbol and said first portion of the object.

13. A method according to claim 12 wherein said visible symbol is a two-dimensional symbol.

14. A method according to claim 12 wherein said relative location is relative to at least one of a position on the object and said visible symbol.

15. A method according to claim 12 further comprising the steps of:
    converting said energy signature and said image of said visible symbol to electronic data in a compatible data format; and
    storing said electronic data and said relative location.

16. A method according to claim 15 wherein said steps of directing, recording and converting occur at a first time, said method further comprising the steps of:
    repeating said steps of directing, recording and converting at a second time that is subsequent to said first time, wherein a current relative location is recorded and a current electronic data is generated at said second time; and
    comparing said electronic data and said relative location from said first time with said current electronic data and said current relative location from said second time.

17. A method according to claim 16 wherein said steps of directing, recording, converting, storing, repeating and comparing are performed using a single device.

18. A method according to claim 15 wherein said steps of directing, recording, converting and storing are performed using a single device.

19. A method according to claim 12 wherein said steps of directing and recording are performed using a single device.

20. A system for identifying and authenticating an object having an x-ray fluorescing taggant placed in a first portion of an object and a visible symbol placed on a second portion of the object, said system comprising:
    first means for impinging x-rays on the object in the vicinity of the first portion thereof wherein said taggant fluoresces with a specific energy signature;
    second means for recording said energy signature, at least one image of said symbol, and a relative location of the first portion of the object, said second means including (i) a first image recording device for recording a first image of said visible symbol using a first field-of-view that is substantially limited to said visible symbol, and (ii) a second image recording device for recording a second image of said visible symbol using a second field-of-view that includes said visible symbol and said first portion of the object;
    third means for storing (i) said energy signature and said image of said visible symbol as electronic data in a compatible data format, and (ii) said relative location; and fourth means for comparing said electronic data and said relative location associated with a first point in time with said electronic data and said relative location associated with a second point in time.

21. A system as in claim 20 wherein said first means, said second means, said third means and said fourth means are incorporated into a single device.

22. A system as in claim 21 wherein said single device is a hand-held device.

* * * * *